(12) United States Patent
Suyama et al.

(10) Patent No.: US 9,421,653 B2
(45) Date of Patent: Aug. 23, 2016

(54) CUTTING PROCESSING DEVICE

(71) Applicant: Roland DG Corporation, Hamamatsu-shi, Shizuoka (JP)

(72) Inventors: Akihiro Suyama, Hamamatsu (JP); Kazuhide Hamamatsu, Hamamatsu (JP)

(73) Assignee: ROLAND DG CORPORATION, Shizuoka (JP)

( * ) Notice: Subject to any disclaimer, the term of this patent is extended or adjusted under 35 U.S.C. 154(b) by 131 days.

(21) Appl. No.: 14/472,478

(22) Filed: Aug. 29, 2014

(65) Prior Publication Data

US 2015/0071724 A1    Mar. 12, 2015

(30) Foreign Application Priority Data

Sep. 12, 2013  (JP) .................. 2013-189469

(51) Int. Cl.

| | |
|---|---|
| *A61C 1/14* | (2006.01) |
| *B23Q 3/06* | (2006.01) |
| *B23C 3/16* | (2006.01) |
| *B23Q 1/52* | (2006.01) |
| *B23Q 39/02* | (2006.01) |
| *A61C 13/00* | (2006.01) |

(52) U.S. Cl.

CPC .............. *B23Q 3/061* (2013.01); *A61C 1/14* (2013.01); *B23C 3/16* (2013.01); *B23Q 1/525* (2013.01); *B23Q 39/028* (2013.01); *A61C 13/0006* (2013.01); *A61C 13/0022* (2013.01); *B23C 2226/18* (2013.01); *Y10T 409/309016* (2015.01)

(58) Field of Classification Search

CPC .............. B23Q 3/061; B23Q 39/028; Y10T 409/30868; Y10T 409/308792; Y10T 409/30896; Y10T 409/309016; Y10T 409/3056; Y10T 409/305656; B23C 2226/18; A61C 1/14; A61C 13/0006; A61C 13/0022

See application file for complete search history.

(56) References Cited

U.S. PATENT DOCUMENTS

| | | | | |
|---|---|---|---|---|
| 4,444,534 | A * | 4/1984 | Bergman ................ | B23Q 1/01 408/235 |
| 5,158,487 | A * | 10/1992 | Varnau .................. | B23Q 3/103 269/902 |
| 8,784,021 | B2 * | 7/2014 | Luksch .............. | A61C 13/0004 269/7 |
| 8,977,381 | B1 * | 3/2015 | Mezzasalma ........... | B23Q 1/25 700/160 |
| 2003/0053875 | A1 * | 3/2003 | Pasquetto ........... | B23Q 1/5437 409/192 |
| 2007/0173182 | A1 * | 7/2007 | Curcher ................ | B23Q 3/062 451/42 |
| 2007/0209185 | A1 * | 9/2007 | Huang .................... | B23P 13/02 29/38 R |
| 2009/0023112 | A1 * | 1/2009 | Ganley ................... | A61C 5/10 433/215 |

(Continued)

FOREIGN PATENT DOCUMENTS

| | | | | |
|---|---|---|---|---|
| DE | 102004013789 | A1 * | 10/2005 | ............ B23Q 3/061 |
| DE | 102008030050 | A1 * | 8/2009 | ......... A61C 13/0022 |

(Continued)

*Primary Examiner* — Sunil K Singh
*Assistant Examiner* — Ryan Rufo
(74) *Attorney, Agent, or Firm* — Keating and Bennett, LLP (57) ABSTRACT

A cutting processing device for performing a cutting process on a cutting target by use of a rotatable tool includes a cutting unit that includes the rotatable tool, a holding tool that holds a plurality of the cutting targets at the same time, and a rotation support unit that rotatably supports the holding tool. The cutting unit is movable with respect to the holding tool.

5 Claims, 5 Drawing Sheets

(56) References Cited

U.S. PATENT DOCUMENTS

| | | | | |
|---|---|---|---|---|
| 2009/0130634 A1* | 5/2009 | Ganley | A61C 13/0022 | 433/206 |
| 2009/0274994 A1* | 11/2009 | Jung | A61C 13/0022 | 433/202.1 |
| 2009/0275000 A1* | 11/2009 | Jung | A61C 13/0004 | 433/223 |
| 2011/0104643 A1* | 5/2011 | Giordano | A61C 13/0022 | 433/203.1 |
| 2012/0068393 A1* | 3/2012 | Van de Vosse | B23Q 1/525 | 269/9 |
| 2012/0148985 A1* | 6/2012 | Jung | A61C 13/08 | 433/212.1 |
| 2012/0214133 A1* | 8/2012 | Jung | A61C 8/005 | 433/174 |

FOREIGN PATENT DOCUMENTS

| | | | | |
|---|---|---|---|---|
| DE | 102011109939 A1 * | 2/2013 | | A61C 13/0022 |
| EP | 1023876 A2 * | 8/2000 | | A61C 13/0022 |
| EP | 1728485 A2 * | 12/2006 | | A61C 7/00 |
| WO | WO 2012/087997 A1 * | 6/2012 | | A61C 13/0022 |

* cited by examiner

CUTTING PROCESSING DEVICE

The present application claims priority from Japanese Patent Application No. 2013-189469 filed on Sep. 12, 2013, which is incorporated by reference herein in its entirety.

BACKGROUND OF THE INVENTION

1. Field of the Invention

The present invention relates to a cutting processing device.

2. Description of the Related Art

Conventionally, cutting processing devices that perform a cutting process on a cutting target by use of a rotatable tool are known. An example of cutting processing device is an artificial tooth processing device that performs a cutting process on an artificial tooth used for implant treatment. By use of the artificial tooth processing device, a dental member formed of a ceramic material such as zirconia or the like or a resin material such as an acrylic material or the like is cut into a desired shape to produce an artificial tooth.

Such an artificial tooth processing device includes a housing; a rotation holding unit that rotatably holds a cutting target, which is a dental member; and a cutting unit that cuts the cutting target held by the holding unit into a desired shape. A dust collection device is provided separately from the artificial tooth processing device. Inside the housing, a processing space is provided. The rotation holding unit and a cutting unit are located in the cutting space. The artificial tooth device is provided with a dust collection tube that couples the processing space inside the housing and the dust collection device. An overall operation of the artificial tooth processing device is controlled by a microcomputer.

The microcomputer controls the rotation holding unit and the cutting unit to be moved in predetermined directions, so that relative positions of the cutting target held by the rotation holding unit and a tool provided in the cutting unit are changed three-dimensionally. Thus, the artificial tooth processing device performs a cutting process on the cutting target.

Cutting chips generated during the cutting process performed on the cutting target are transferred to the dust collection device via the dust collection tube. Thus, the cutting chips are removed from the processing space inside the housing.

Figure 6:
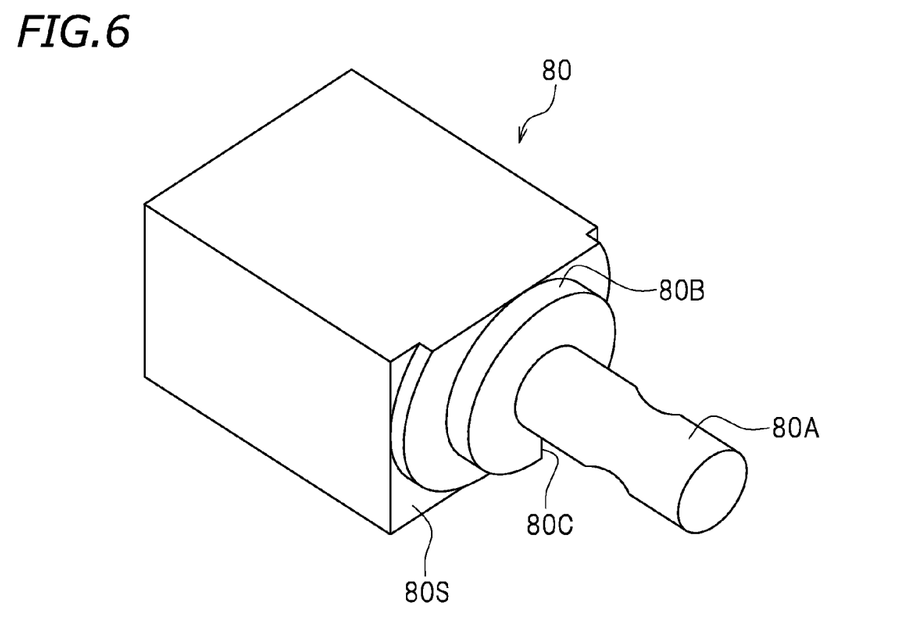
FIG. 6 is a perspective view showing a structure of a cutting target.
Figure 7:
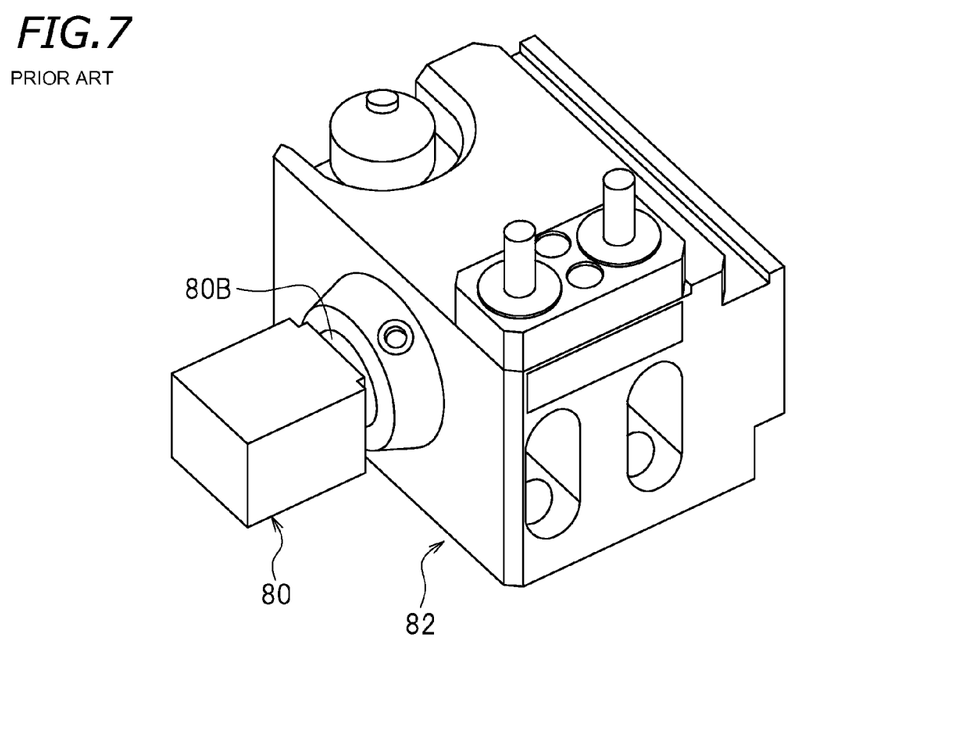
FIG. 7 is a perspective view showing a state where a cutting target is attached to a rotation holding unit in the conventional art.

For performing a cutting process on a cutting target by use of an artificial tooth processing device, as shown in, for example, FIG. 6, a pin 80A is attached to a predetermined surface 80S of a generally parallelepiped cutting target 80 via a plate-shaped member 80B. As shown in FIG. 7, the pin 80A is rotatably held by a rotation holding unit 82, so that one cutting target 80 is held by the rotation holding unit 82.

Therefore, in an operation of producing a plurality of artificial teeth of the same shape, each time one artificial tooth is to be produced, a cutting target 80 needs to be newly held by the rotation holding unit 82. This causes a problem of imposing a heavy load on the operator.

SUMMARY OF THE INVENTION

Preferred embodiments of the present invention provide a cutting processing device capable of holding a plurality of cutting targets.

A cutting processing device according to a preferred embodiment of the present invention is a cutting processing device for performing a cutting process on a cutting target by use of a rotatable tool. The cutting processing device includes a cutting unit that includes the rotatable tool, a holding tool configured to hold a plurality of the cutting targets at the same time, and a rotation support unit configured to rotatably support the holding tool. The cutting unit is configured to move with respect to the holding tool.

According to a preferred embodiment of the present invention, the holding tool preferably is configured to hold a plurality of cutting targets at the same time. Therefore, a plurality of products of the same shape are capable of being produced by one cycle of operation. Therefore, in the case where a plurality of products of the same shape are to be produced, the frequency with which the operation of causing a cutting target to be newly held by the holding tool is performed is decreased. This significantly reduces the load on the operator.

According to a preferred embodiment of the present invention, the holding tool extends in a direction in which a rotation axis of the holding tool extends away from the rotation support unit, and the holding tool includes a plurality of securing portions that are located along the rotation axis of the holding tool and hold the cutting targets.

According to a preferred embodiment of the present invention, pins to be secured to the securing portions are respectively attached to the cutting targets, and the securing portions include holes engageable with the pins inserted thereinto.

According to a preferred embodiment of the present invention, in a state in which the cutting targets are held by the holding tool, the cutting targets or the pins overlap the rotation axis of the holding tool.

According to a preferred embodiment of the present invention, the cutting targets each include, attached thereto, a plate-shaped member that includes a cut-off portion and is located between the cutting target and the pin, and the holding tool includes protrusions each engageable with the cut-off portion.

According to a preferred embodiment of the present invention, the holding tool includes a support shaft supportable by the rotation support unit, a plate-shaped member connected to one end of the support shaft, and a securing member that is connected to the plate-shaped member and extends in a direction in which the rotation axis of the holding tool extends away from the support shaft, and the securing portions are located at the securing member.

According to a preferred embodiment of the present invention, the securing portions include first, second, third, fourth and fifth securing portions. The first securing portion, the second securing portion, the third securing portion, the fourth securing portion and the fifth securing portion are arranged along the rotation axis of the holding tool in this order. The first securing portion and the third securing portion are spaced from each other by a first gap. The third securing portion and the fifth securing portion are spaced from each other by the first gap. The first securing portion and the second securing portion are spaced from each other by a second gap that is smaller than the first gap. The second securing portion and the fourth securing portion are spaced from each other by the second gap. The fourth securing portion and the fifth securing portion are spaced from each other by the second gap. In a case in which the cutting targets are first cutting targets, the first cutting targets are respectively secured to the first securing portion, the third securing portion and the fifth securing portion. In a case in which the cutting targets are second cutting targets that are smaller than the first cutting targets, the second cutting targets are respectively secured to the first securing portion, the second securing portion, the fourth securing portion and the fifth securing portion.

A cutting processing device according to various preferred embodiments of the present invention, which has the above-described structure, is configured to hold a plurality of cutting targets at the same time and therefore provides an superb effect of improving workability.

The above and other elements, features, steps, characteristics and advantages of the present invention will become more apparent from the following detailed description of the preferred embodiments with reference to the attached drawings.

DETAILED DESCRIPTION OF THE PREFERRED EMBODIMENTS

Figure 1:
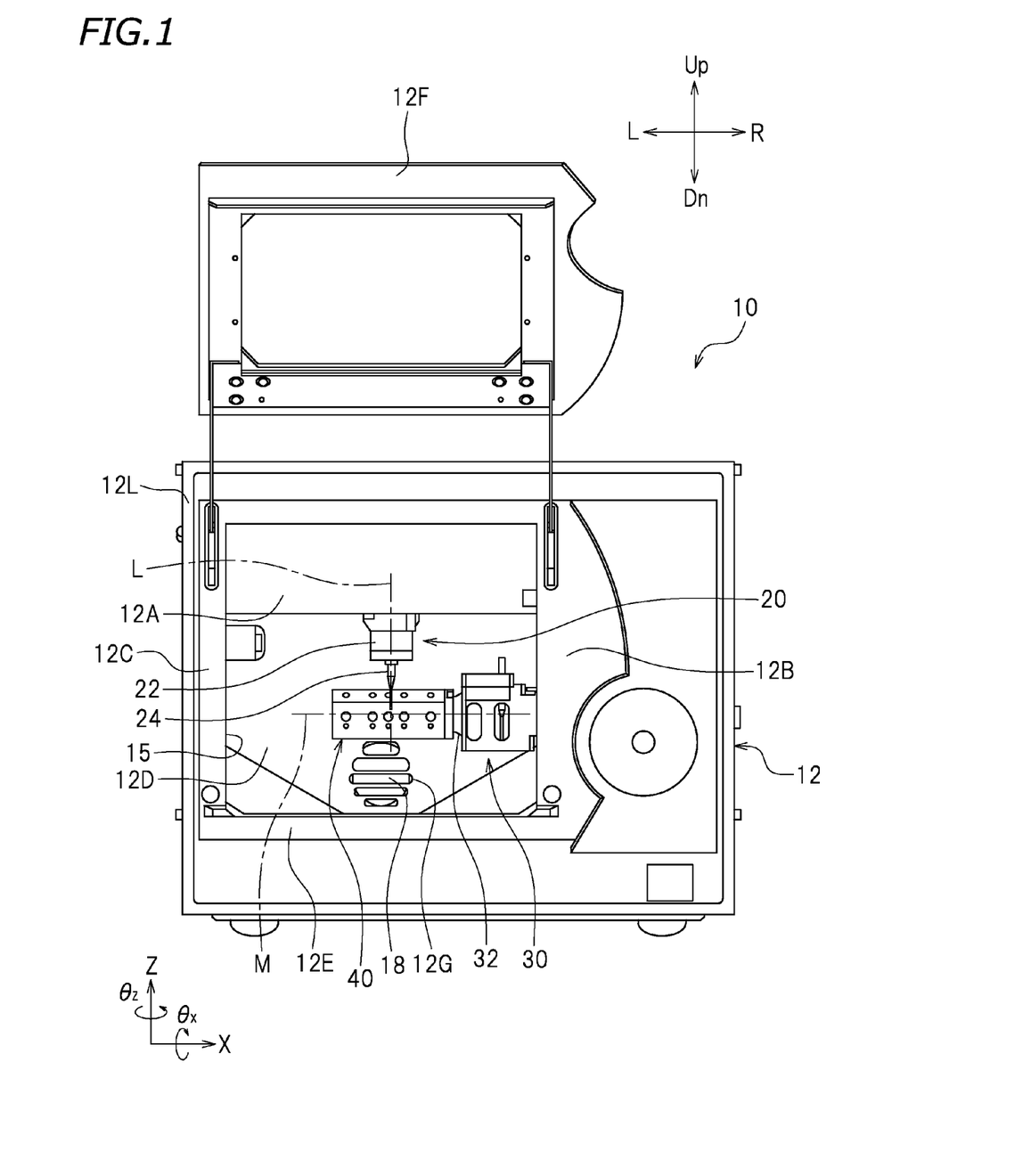
FIG. 1 is a front view showing a structure of an artificial tooth processing device according to a preferred embodiment of the present invention.

Hereinafter, preferred embodiments of a cutting processing device according to the present invention will be described with reference to the drawings. As shown in FIG. 1, a cutting processing device according to a preferred embodiment of the present invention preferably is an artificial tooth processing device 10 that performs a cutting process on an artificial tooth. A case where the artificial processing device is the artificial tooth processing device 10 will be described below, but the present invention is not limited to being applied to such a type of device.

Figure 3:
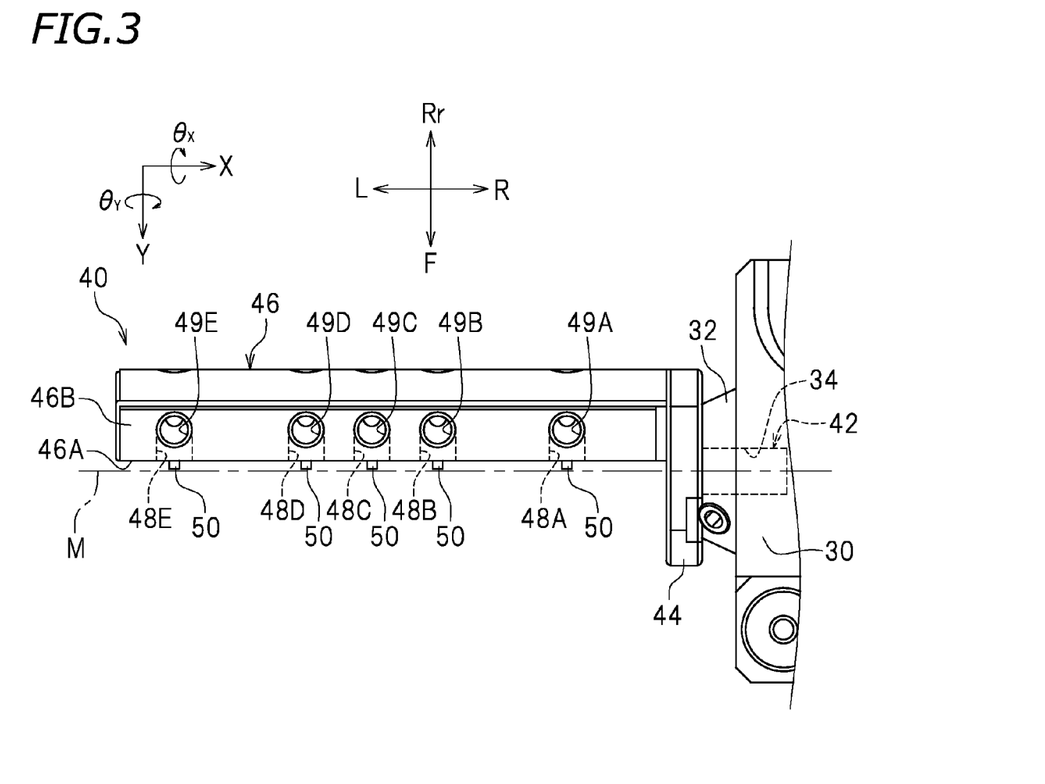
FIG. 3 is a plan view showing the holding tool attached to a rotation support unit according to a preferred embodiment of the present invention.

In the following description, unless otherwise specified, left, right, top and bottom in FIG. 1 are respectively left, right, top and bottom of the artificial tooth processing device 10. Left, right, top and bottom in FIG. 3 are respectively left, right, rear and front of the artificial tooth processing device 10. In the figures, letters F, Rr, L, R, Up and Dn respectively indicate front, rear, left, right, up and down. In the figures, letter X represents an X axis and a left-right direction. In the figures, letter Y represents a Y axis and a front-rear direction. In the figures, letter Z represents a Z axis and an up-down direction. Reference signs $\theta_X$, $\theta_Y$ and $\theta_Z$ respectively represent rotation directions around the X axis, the Y axis and the Z axis. In this preferred embodiment, the X axis, the Y axis and the Z axis are set such that either one thereof is perpendicular to the other two thereof. It should be noted that it is sufficient that the X axis, the Y axis and the Z axis are set such that either one thereof intersects the other two thereof. These directions are merely set for the purpose of illustration and do not limit the manner in which the artificial tooth processing device 10 is installed.

As shown in FIG. 1, the artificial tooth processing device 10 preferably includes a housing 12, a cutting unit 20, a rotation support unit 30, and a holding tool 40.

As shown in FIG. 1, the housing 12 includes a top wall 12A, a right wall 12B, a left wall 12C, a rear wall 12D, a bottom wall 12E, and a door 12F. The door 12F is attached to a front surface 12L of the housing 12. The door 12F is pivoted upward and downward to be opened and closed. Inside the housing 12, a processing space 15 is provided. The processing space 15 is a closed space enclosed by the top wall 12A, the right wall 12B, the left wall 12C, the rear wall 12D, the bottom wall 12E and the door 12F. In the processing space 15, a cutting process is performed on a cutting target 80 (see FIG. 6).

The cutting unit 20 performs a cutting process on the cutting target 80 (see FIG. 6). As shown in FIG. 1, the cutting unit 20 is provided on the top wall 12A of the housing 12. The cutting unit 20 is movable with respect to the holding tool 40. The cutting unit 20 includes a spindle 22 and a tool 24 detachably attached to the spindle 22. The cutting unit 20 includes a movable member (not shown) that is movable in the X axial direction and the Z axial direction in an XYZ orthogonal coordinate system. The movable member is movable in the left-right direction and in the up-down direction. The spindle 22 is secured to the movable member. The spindle 22 is located above the holding tool 40. The movable member moves in the X axial direction and the Z axial direction, and accordingly the spindle 22 moves in the X axial direction and the Z axial direction. The spindle 22 rotates the tool 24. The spindle 22 rotates the tool 24 around the Z axis. A rotation axis L of the spindle 22 overlaps a rotation axis M of the holding tool 40 described later as seen from the front.

The rotation support unit 30 rotatably supports the holding tool 40. The rotation support unit 30 is provided on the right wall 12B of the housing 12. The rotation support unit 30 includes a movable member (not shown) that is movable in the Y axial direction in the XYZ orthogonal coordinate system. The movable member is movable in the front-rear direction. The rotation support unit 30 includes a rotatable member 32. The holding tool 40 is detachably attached to the rotatable member 32. The rotatable member 32 is rotatable around the X axis. The rotatable member 32 rotates around the X axis, and accordingly the holding tool 40 rotates around the X axis. The rotation support unit 30 moves in the Y axial direction, and accordingly the holding tool 40 moves in the Y axial direction.

Figure 2:
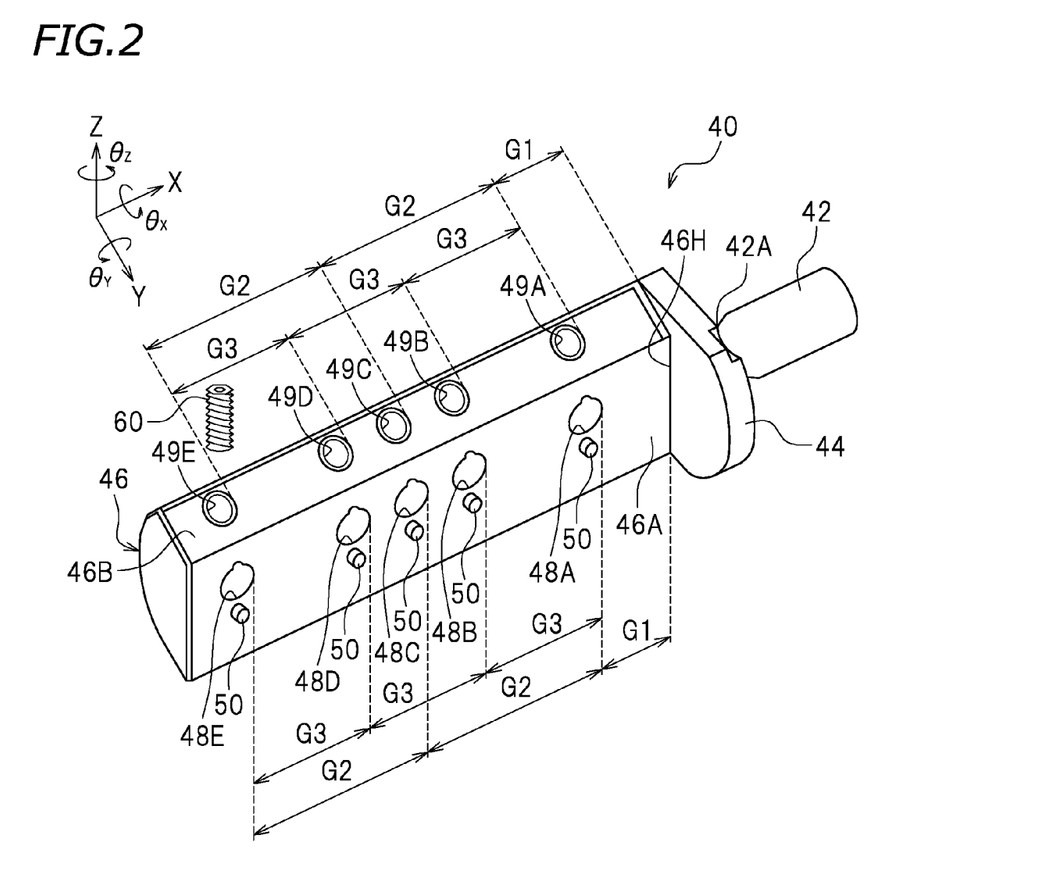
FIG. 2 is a perspective view showing a structure of a holding tool according to a preferred embodiment of the present invention.
Figure 4:
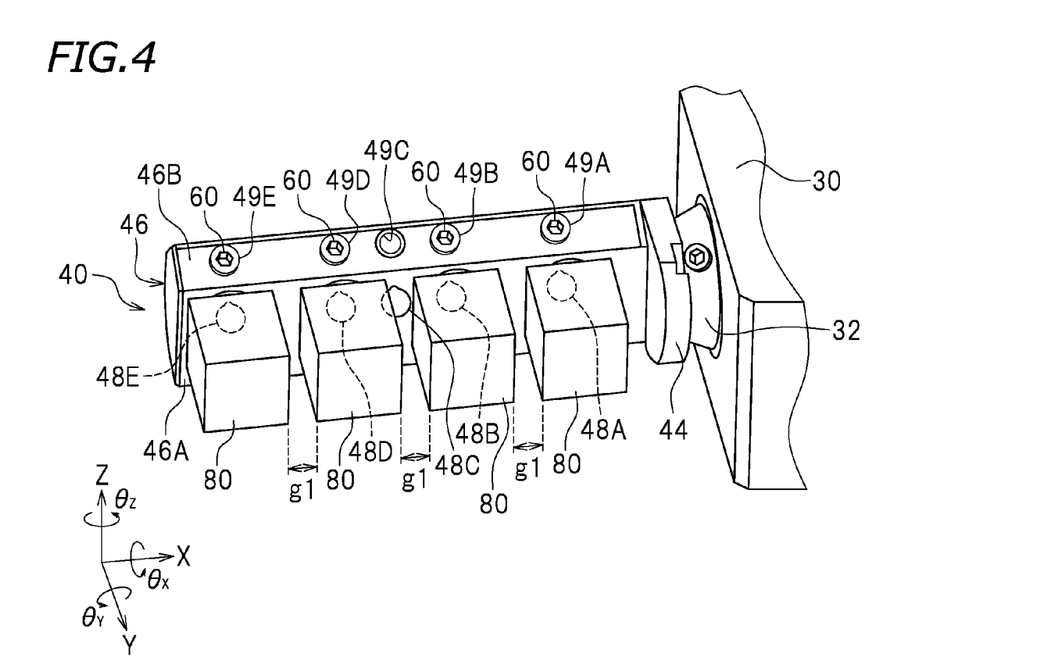
FIG. 4 is a perspective view showing a state where four cutting targets are held by the holding tool according to a preferred embodiment of the present invention.

As shown in FIG. 2, the holding tool 40 preferably includes five securing portions 48A through 48E, for example. The securing portions 48A through 48E each hold the cutting target 80 (see FIG. 6). As shown in FIG. 3, the securing portions 48A through 48E are located along the rotation axis M of the holding tool 40. The holding tool 40 extends in a direction in which the rotation axis M of the holding tool 40 extends away from the rotation support unit 30. The securing portion 48A is closest to the rotation support unit 30, and the securing portion 48E is farthest from the rotation support unit 30. The holding tool 40 extends in the left-right direction. The holding tool 40 extends in the X axial direction. As shown in FIG. 4, the holding tool 40 holds a plurality of cutting targets 80 at the same time.

As shown in FIG. 2, the holding tool 40 includes a support shaft 42, a plate-shaped member 44, and a securing member 46. As shown in FIG. 3, the support shaft 42 is detachably supported by the rotation support unit 30. The support shaft 42 extends along the rotation axis M of the holding tool 40. The support shaft 42 extends in the X axial direction. The support shaft 42 is inserted into a holding tool insertion opening 34 that is located at a rotation center of the rotation support unit 30. As a result, the holding tool 40 is rotatable around the X axis as being centered around the rotation axis M of the holding tool 40. As shown in FIG. 2, the plate-shaped member 44 is connected to one end 42A of the support shaft 42.

As shown in FIG. 3, the securing member 46 is connected to the plate-shaped member 44. The securing member 46 extends in a direction in which the rotation axis M of the holding tool 40 extends away from the support shaft 42. The securing member 46 extends in the X axial direction. The securing member 46 is located at such a position that does not overlap the rotation axis M of the holding tool 40. In the state shown in FIG. 3, a side surface 46A of the securing member 46 is located rearward with respect to the rotation axis M of the holding tool 40. When the holding tool 40 rotates, the securing member 46 does not overlap the rotation axis M of the holding tool 40. The securing member 46 is located away from the rotation axis M of the holding tool 40 in a direction perpendicular to the rotation axis M.

As shown in FIG. 2, the securing portions 48A through 48E are located at the side surface 46A of the securing member 46. The securing portions 48A through 48E are respectively engageable with pins 80A (FIG. 6) attached to the cutting targets 80 (FIG. 6) in the state where the pins 80A are inserted into the securing portions 48A through 48E. The pins 80A of the cutting targets 80 are respectively secured to the securing portions 48A through 48E. In this preferred embodiment, the securing portions 48A through 48E are each a hole, for example.

As shown in FIG. 3, the securing portions 48A, 48B, 48C, 48D and 48E are arranged in this order in the direction in which the rotation axis M of the holding tool 40 extends away from the support shaft 42. The securing portions 48A, 48B, 48C, 48D and 48E are arranged in this order along the rotation axis M of the holding tool 40.

As shown in FIG. 2, the securing portion 48A and one end 46H of the securing member 46 are spaced from each other by gap G1. The securing portion 48A and the plate-shaped member 44 are spaced from each other by gap G1. Gap G1 is such a length that prevents the cutting target 80 from contacting the plate-shaped member 44 when the cutting target 80 is secured to the securing portion 48A. The securing portion 48C and the securing portion 48A are spaced from each other by gap G2. Gap G2 is larger than gap G1. The securing portion 48E and the securing portion 48C are spaced from each other by gap G2. The securing portion 48A, the securing portion 48C and the securing portion 48E are spaced from each other by an equal gap G2.

As shown in FIG. 2, the securing portion 48B and the securing portion 48A are spaced from each other by gap G3. Gap G3 is smaller than gap G2. Gap G3 is larger than gap G1. The securing portion 48D and the securing portion 48B are spaced from each other by gap G3. The securing portion 48E and the securing portion 48D are spaced from each other by gap G3. The securing portion 48A, the securing portion 48B, the securing portion 48D and the securing portion 48E are spaced from each other by an equal gap G3.

As shown in FIG. 2, five screw holes 49A through 49E are provided at a top surface 46B of the securing member 46. Screws 60 (only one is shown in FIG. 2) are insertable into the screw holes 49A through 49E. The screw holes 49A through 49E are respectively in communication with the securing portions 48A through 48E. The pins 80A inserted into the securing portions 48A through 48E are secured by the screws 60 inserted into the screw holes 49A through 49E.

As shown in FIG. 3, the screw holes 49A, 49B, 49C, 49D and 49E are arranged in this order in the direction in which the rotation axis M of the holding tool 40 extends away from the support shaft 42. The screw hole 49A is closest to the support shaft 42, and the screw holes 49E is farthest from the support shaft 42. The screw holes 49A, 49B, 49C, 49D and 49E are arranged in this order along the rotation axis M of the holding tool 40.

As shown in FIG. 2, the screw hole 49A and the one end 46H of the securing member 46 are spaced from each other by gap G1. The screw hole 49A and the plate-shaped member 44 are spaced from each other by gap G1. The screw hole 49C and the screw hole 49A are spaced from each other by gap G2. The screw hole 49E and the screw hole 49C are spaced from each other by gap G2. The screw hole 49A, the screw hole 49C and the screw hole 49E are spaced from each other by an equal gap G2.

As shown in FIG. 2, the screw hole 49B and the screw hole 49A are spaced from each other by gap G3. The screw hole 49D and the screw hole 49B are spaced from each other by gap G3. The screw hole 49E and the screw hole 49D are spaced from each other by gap G3. The screw hole 49A, the screw hole 49B, the screw hole 49D and the screw hole 49E are spaced from each other by an equal gap G3.

As shown in FIG. 2, the holding tool 40 includes protrusions 50 each engageable with a cut-off portion 80C (see FIG. 6) of a plate-shaped member 80B attached to the cutting target 80 described later. The protrusions 50 are located on the securing member 46. The protrusions 50 are respectively located in the vicinity of the securing portions 48A through 48E. In the state shown in FIG. 2, the protrusions 50 are located below the securing portions 48A through 48E. A width of each protrusion 50 of the holding tool 40 is preferably the same or substantially the same as a width of each cut-off portion 80C. For securing the cutting targets 80 to the securing portions 48A through 48E, the cut-off portions 80C and the protrusions 50 are engaged with each other. Thus, the cutting targets 80 secured to the securing portions 48A through 48E are directed in the same direction.

As shown in FIG. 6, the pin 80A and the plate-shaped member 80B are attached to the cutting target 80. The plate-shaped member 80B is located between the cutting target 80 and the pin 80A. The plate-shaped member 80B includes the cut-off portion 80C.

As shown in FIG. 4, the pins 80A (see FIG. 6) attached to the cutting targets 80 of a predetermined size are inserted into the securing portions 48A, 48B, 48D and 48E, and then the screws 60 are inserted into the screw holes 49A, 49B, 49D and 49E. As a result, the cutting targets 80 of the predetermined size are secured to the holding tool 40 in the state where adjacent cutting targets 80 among such cutting targets 80 are spaced from each other by gap g1.

Figure 5:
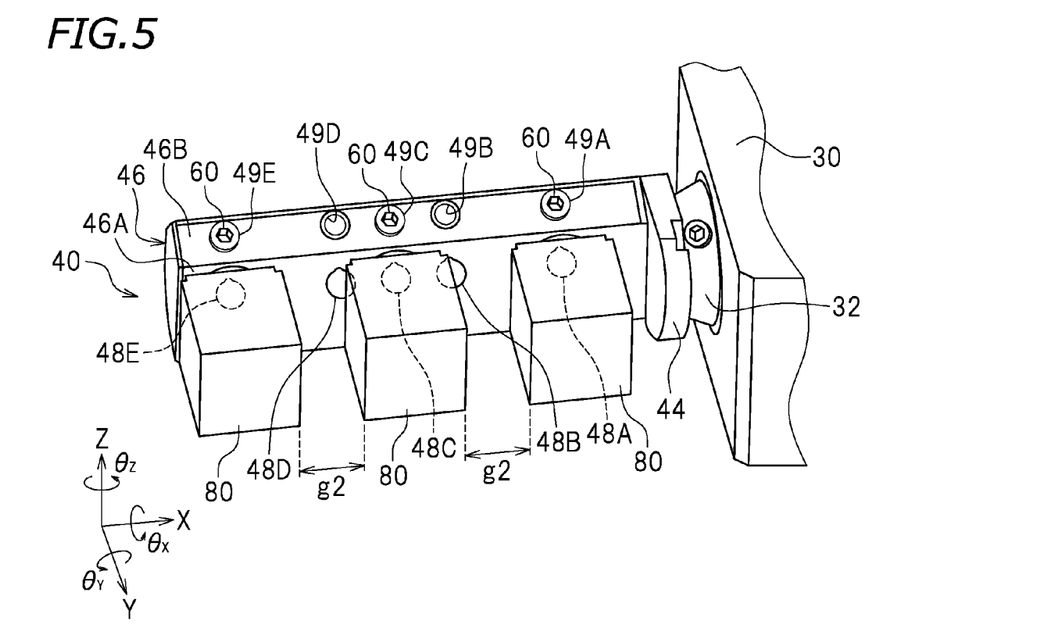
FIG. 5 is a perspective view showing a state where three cutting targets are held by the holding tool according to a preferred embodiment of the present invention.

As shown in FIG. 5, the pins 80 (see FIG. 6) attached to cutting targets 80 larger than the predetermined size are inserted into the securing portions 48A, 48C and 48E, and then the screws 60 are inserted into the screw holes 49A, 49C and 49E. As a result, the cutting targets 80 larger than the predetermined size are secured to the holding tool 40 in the state where adjacent cutting targets 80 among such cutting targets 80 are spaced from each other by gap g2. Gap g2 is larger than gap g1.

In the state where the cutting targets 80 are held by the holding tool 40, the cutting targets 80 or the pins 80A overlap the rotation axis M of the holding tool 40.

As shown in FIG. 1, a dust collection device (not shown) provided separately from the artificial tooth processing device 10 is connected to the artificial tooth processing device 10 via a dust collection tube 18. The dust collection tube 18 is coupled to an opening 12G provided in the rear wall 12D of the housing 12. Cutting chips in the processing space 15 flow to the dust collection device via the opening 12G the dust collection tube 18.

An overall operation of the artificial tooth processing device 10 is controlled by a microcomputer (not shown). The microcomputer is connected to, for example, a personal computer separately provided. From the personal computer, various types of data including data representing the shape of the artificial teeth to be produced is input to the microcomputer.

The tool 24 is moved in the X axial direction and the Z axial direction by the control of the microcomputer, and concurrently, the cutting targets 80 held by the holding tool 40 are moved in the Y axial direction. The relative positions of the tool 24 attached to the spindle 22 and the cutting targets 80 held by the holding tool 40 can be changed in any direction among the X axial direction, the Y axial direction and the Z axial direction.

Now, a case where artificial teeth are produced from the cutting targets 80 by use of the artificial tooth processing device 10 will be described.

First, various types of correction values are acquired at a predetermined timing when, for example, the artificial tooth processing device 10 is installed. Cutting targets 80 having a size suitable to the size of the artificial teeth to be produced by the cutting process are held by the holding tool 40. In an example where four cutting targets 80 are to be secured to the securing portions 48A, 48B, 48D and 48E but adjacent cutting targets 80 among such cutting targets 80 contact each other, or the four cutting targets 80 cannot be distanced from each other by a predetermined gap, three cutting targets 80 are secured to the securing portions 48A, 48C and 48E. The "predetermined gap" is a minimum possible length at which a flaw may not possibly occur during the cutting process performed on a predetermined cutting target 80; for example, a flaw such that when a cutting process is performed on a predetermined cutting target 80, the tool 24 contacts another cutting target 80 adjacent to the predetermined cutting target 80.

Hereinafter, a case where the cutting targets 80 are held in the securing portions 80A, 80B, 80D and 80E will be described.

For example, the pins 80A of four cutting targets 80 are respectively inserted into the securing portions 48A, 48B, 48D and 48E to engage the protrusions 50 with the cut-off portions 80C of the plate-shaped members 80B attached to the cutting targets 80.

Then, the screws 60 are respectively inserted into the screw holes 49A, 49B, 49D and 49E to secure the four cutting targets 80 to the securing member 46. In this manner, the four cutting targets 80 are held by the holding tool 40.

Next, the support shaft 42 of the holding tool 40 holding the four cutting targets 80 is inserted into the holding tool insertion opening 34 provided in the rotatable member 32 of the rotation support unit 30. As a result, the holding tool 40 is rotatably supported by the rotation support unit 30. The door 12F of the housing 12 is closed, and the artificial tooth processing device 10 is started.

Then, cutting processing data on the artificial teeth, position information on the cutting targets 80 held by the holding tool 40 and the like are input from the personal computer (not shown) provided separately from the artificial tooth processing device 10 to the microcomputer (not shown).

When an operator issues an instruction to start a cutting process via an operation panel (not shown), the cutting process on the cutting targets 80 is started by control of the microcomputer (not shown). The cutting process on the cutting targets 80 is performed based on the input processing data and position information on the cutting targets 80, the correction values for the artificial tooth processing device 10 and the like. The cutting process is performed sequentially on the four cutting targets 80, for example, from the cutting target 80 located at the leftmost position (the cutting target 80 farthest from the support shaft 42).

As described above, in the artificial tooth processing device 10 according to a preferred embodiment of the present invention, the holding tool 40 capable of holding a plurality of cutting targets 80 is detachably attached to the rotatable member 32 of the rotation support unit 30.

The securing member 46 extends in the direction in which the rotation axis M of the holding tool 40 extends away from the support shaft 42. The securing member 46 includes the securing portions 48A, 48B, 48C, 48D and 48E, which are arranged in this order in the direction in which the rotation axis M of the holding tool 40 extends away from the support shaft 42.

At the top surface 46B of the securing member 46, screw holes 49A, 49B, 49C, 49D and 49E are arranged in this order in the direction in which the rotation axis M of the holding tool 40 extends away from the support shaft 42.

The pins 80A inserted into the securing portions 48A through 48E are secured by the screws 60 inserted into the screw holes 49A through 49E. Thus, three or four cutting targets 80 preferably are held by the holding tool 40. As can be seen, in the artificial tooth processing device 10, three or four cutting targets 80 are easily held by the holding tool 40. As a result, three or four artificial teeth having the same shape are produced at the same time. This improves the workability as compared with the artificial tooth processing device of the conventional art.

The above-described preferred embodiment may be modified as described in (1) through (7) below.

(1) The securing member 46 of the holding tool 40 may include securing portions and screw holes at the side surface 46A and the top surface 46B such that five or more cutting targets 80 are capable of being secured while being located with an equal gap, for example. Alternatively, the securing member 46 of the holding tool 40 may include securing portions and screw holes at the side surface 46A and the top surface 46B such that three or four cutting targets 80 are capable of being secured while not being located with an equal gap. Still alternatively, the securing member 46 of the holding tool 40 may include securing portions and screw holes at the side surface 46A and the top surface 46B such that five or more cutting targets 80 are secured while being distanced from each other by such a gap that does not cause any flaw or inconvenience in the cutting process.

(2) The securing member 46 may be located at a position that overlaps the rotation axis M of the holding tool 40. In the state shown in FIG. 3, the side surface 46A of the securing member 46 may be located on the rotation axis M of the holding tool 40. Alternatively, the side surface 46A of the securing member 46 may be located forward with respect to the rotation axis M of the holding tool 40.

(3) A cutting target 80 having a size that cannot be held by the holding tool 40 may be directly supported by the rotation support member 30 in the state where the pin 80A is directly inserted into the holding tool insertion opening 34 provided in the rotatable member 32.

(4) In the above-described preferred embodiment, the rotation support unit 30 preferably is movable in the Y axial direction, whereas the cutting unit 20 preferably is movable in the X axial direction and the Z axial direction. The present invention is not limited to this. For example, the rotation support unit 30 may be movable in the X axial direction and the Y axial direction, whereas the cutting unit 20 may be movable in the Z axial direction. Alternatively, the rotation support unit 30 may not be movable, whereas the cutting unit 20 may be movable in the X axial direction, the Y axial direction and the Z axial direction. As long as the relative positions of the cutting target(s) 80 held by the holding tool 40 and the tool 24 attached to the spindle 22 of the cutting unit 20 are changed three-dimensionally, the rotation support unit 30 and the cutting unit 20 may be movable in any manner.

(5) In the above preferred embodiment, the holding tool 40 extends in the X axial direction. Alternatively, the holding tool 40 may extend in the Y axial direction.

(6) In the above preferred embodiment, the spindle 22 is preferably located above the holding tool 40. The present invention is not limited to this. For example, the spindle 22 may be located to the side of the holding tool 40, or may be located below the holding tool 40.

The above preferred embodiment and modifications (1) through (6) may be combined in any appropriate manner.

Various preferred embodiments of the present invention are preferably usable for performing a cutting process on a cutting target such as, for example, an artificial tooth used for implant treatment.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:
1. A cutting processing device for performing a cutting process on a cutting target by use of a rotatable tool, the cutting processing device comprising:
 a cutting unit that includes the rotatable tool;
 a holding tool configured to hold a plurality of the cutting targets at the same time; and
 a rotation support unit configured to rotatably support the holding tool; wherein
 the cutting unit is configured to move with respect to the holding tool
 the holding tool extends in a direction in which a rotation axis of the holding tool extends away from the rotation support unit;
 the holding tool includes a plurality of securing portions that are located along the rotation axis of the holding tool and hold the cutting targets
 the securing portions include first, second, third, fourth and fifth securing portions;
 the first securing portion, the second securing portion, the third securing portion, the fourth securing portion and the fifth securing portion are arranged along the rotation axis of the holding tool in this order;
 the first securing portion and the third securing portion are spaced from each other by a first gap;
 the third securing portion and the fifth securing portion are spaced from each other by the first gap;
 the first securing portion and the second securing portion are spaced from each other by a second gap that is smaller than the first gap;
 the second securing portion and the fourth securing portion are spaced from each other by the second gap;
 the fourth securing portion and the fifth securing portion are spaced from each other by the second gap;
 in a case in which the cutting targets are first cutting targets, the first cutting targets are respectively secured to the first securing portion, the third securing portion and the fifth securing portion; and
 in a case in which the cutting targets are second cutting targets that are smaller than the first cutting targets, the second cutting targets are respectively secured to the first securing portion, the second securing portion, the fourth securing portion and the fifth securing portion.

2. A cutting processing device according to claim 1, wherein:
 pins to be secured to the securing portions are respectively attached to the cutting targets; and
 the securing portions include holes engageable with the pins inserted thereinto.

3. A cutting processing device according to claim 2, wherein in a state in which the cutting targets are held by the holding tool, the cutting targets or the pins overlap the rotation axis of the holding tool.

4. A cutting processing device according to claim 2, wherein:
 the cutting targets each include, attached thereto, a plate-shaped member that includes a cut-off portion and is located between the cutting target and the pin; and
 the holding tool includes protrusions each engageable with the cut-off portion.

5. A cutting processing device according to claim 1, wherein:
 the holding tool includes a support shaft supportable by the rotation support unit, a plate-shaped member connected to one end of the support shaft, and a securing member that is connected to the plate-shaped member and extends in a direction in which the rotation axis of the holding tool extends away from the support shaft; and
 the securing portions are located at the securing member.

\* \* \* \* \*